Dec. 30, 1941. B. BROOKS ET AL Plant Pat. 498

APRICOT

Filed July 30, 1940

INVENTOR

Bert Brooks and
Glenn M Brooks

By T. J. Geisler
and H. Geisler

ATTORNEYS

Patented Dec. 30, 1941

Plant Pat. 498

UNITED STATES PATENT OFFICE

498

APRICOT

Bert Brooks and Glenn M. Brooks, Lafayette, Oreg.

Application July 30, 1940, Serial No. 348,533

1 Claim. (Cl. 47—62)

This apricot differs in size and color from any other apricot known to us. Its color is more like that of a peach than the color of an ordinary apricot. This apricot is also much larger than the average apricot, being thus similar in size to that of a small ordinary peach.

The texture of our apricot is finer, and its meat is firmer than that of ordinary apricots, the term "ordinary apricot" is to be understood as referring to all other well-known varieties, for example, Riland, Moorpark, Perfection, Gilbert, Lewis, Chinese and Royal.

Our variety also contains a much larger sugar content, than all other varieties of apricots known to us. We had a test made of our apricot as to sugar content and were informed that the sugar content of our apricot was greater by approximately 10% than that of other apricots. A characteristic of our apricot is that it ripens several days ahead of the average apricot, and usually ripens earlier than the peach or plum, or any of the soft fruits, except the cherry.

A further characteristic of our variety of apricot is that the fruit after ripening stays longer on the tree than the ordinary peach; while the ordinary apricot tends to drop from the tree much earlier than the ordinary peach.

A further characteristic of our apricot is that it ripens evenly, while the ordinary apricot tends to ripen on one side more than the other.

A further characteristic of our apricot is that its pit is relatively smaller in proportion to the size of the apricot; and the pit is free so that it may be easily removed.

Due to the texture and greater sugar content of our apricot, it keeps much longer than the ordinary apricot.

The accompanying drawing was made from one of our apricots, and reproduces the same in its natural colors. The figures shown being as follows.

Figure 1:
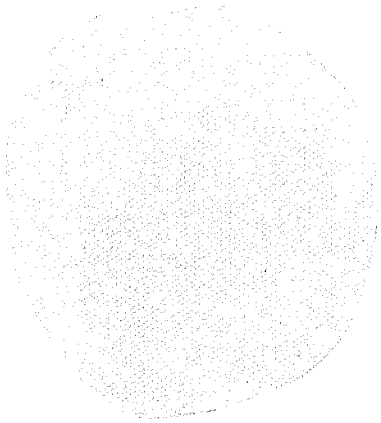
Figure 1 shows one side of our apricot.
Figure 3:
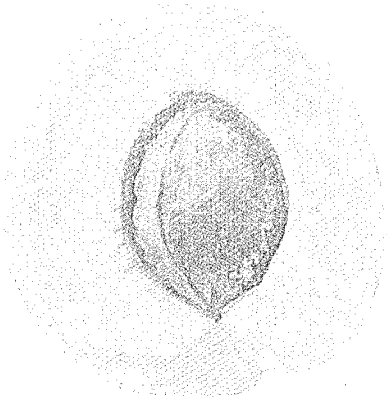
Figure 3 shows one of our apricots cut in half, thus illustrating the form of its pit.
Figure 2:
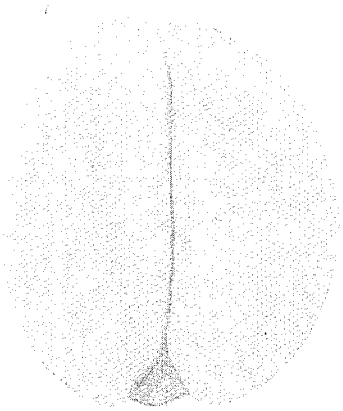
Figure 2 shows a side of our apricot normal to the side shown by Figure 1.

As will be noted from Figure 3, the pit of the fruit is free and thus is easily removed. Our apricot is of a reddish color, and such is also the color of its meat as shown by Figure 3.

Our variety of apricot originated in a seedling tree grown in Homedale, Idaho. The tree when discovered by us was approximately six years old and had borne fruit every year except for two years when its growth was interfered with by frost conditions. We propagated the tree by cutting buds from it and grafting these on a seedling, preferably a peach seedling. All trees propagated by us in this manner produced fruit which had all the characteristics above described.

Propagation of the tree may possibly also be made by cutting and by grafting, but in our opinion the best and surest method of propagation is by a bud taken from a tree reproduced by bud and grafting method traceable back to the original tree. The propagation so made by us has continuously produced fruit of the same character as that grown by the original tree.

Because of the greater sugar content of our apricot, it excels other varieties for drying; and the size of our apricot, and firmness of its meat makes it a better apricot for shipping.

We claim:

A new variety of apricot as shown and described, characterized in that the fruit is of unusually large size, its skin has a reddish exterior tint, its meat also has a reddish tint, and is firm, and the fruit has a tree pit.

BERT BROOKS.
GLENN M. BROOKS.